(12) United States Patent
Elhard et al.

(10) Patent No.: US 6,689,619 B2
(45) Date of Patent: *Feb. 10, 2004

(54) SOLVENT-ACTIVATED COLOR-FORMING COMPOSITIONS

(75) Inventors: Joel D. Elhard, Hilliard, OH (US); Richard P. Heggs, Dublin, OH (US)

(73) Assignee: Battelle Memorial Institute, Columbus, OH (US)

( * ) Notice: Subject to any disclaimer, the term of this patent is extended or adjusted under 35 U.S.C. 154(b) by 126 days.

This patent is subject to a terminal disclaimer.

(21) Appl. No.: 09/843,451

(22) Filed: Apr. 26, 2001

(65) Prior Publication Data

US 2002/0001847 A1 Jan. 3, 2002

Related U.S. Application Data

(63) Continuation-in-part of application No. 09/557,733, filed on Apr. 26, 2000.
(51) Int. Cl.$^7$ ................................................ G01N 25/56
(52) U.S. Cl. .................... 436/166; 436/169; 422/58; 473/378; 73/73
(58) Field of Search ............................. 422/56, 58, 61; 436/164, 166, 169; 473/378; 73/73

(56) References Cited

U.S. PATENT DOCUMENTS

| | | | |
|---|---|---|---|
| 3,669,711 A | 6/1972 | Kimura et al. |
| 3,819,396 A | 6/1974 | Vincent et al. |
| 3,821,010 A | 6/1974 | Vincent et al. |
| 4,302,393 A | 11/1981 | Garner et al. |
| 5,130,290 A | 7/1992 | Tanimoto |
| 5,431,697 A | 7/1995 | Kamata |
| 5,501,945 A | 3/1996 | Kanakkanatt |
| 5,823,891 A | 10/1998 | Winskowicz |
| 5,938,544 A | 8/1999 | Winskowicz |
| 6,071,853 A | 6/2000 | Kirk et al. |

*Primary Examiner*—Lyle A. Alexander
(74) *Attorney, Agent, or Firm*—Klaus H. Wiesmann; Barry S. Bissell (57) ABSTRACT

The present invention provides an object, which, in its outer surface contains a color-forming composition which comprises a solvent-absorbing material that is generally a polymer; a color-former compounded with the solvent-absorbing material, where the color-former functions as a metal chelating agent; and metal ions capable of forming a chelate complex with the color-former as the solvent-absorbing material absorbs a solvent, resulting in a detectable color change of the composition. The present invention also provides a method for indicating exposure of the color-forming composition to a solvent, wherein the color-forming composition is to be used on the outside surface of objects.

21 Claims, 4 Drawing Sheets

SOLVENT-ACTIVATED COLOR-FORMING COMPOSITIONS

This application is a continuation-in-part of U.S. patent application Ser. No. 09/557,733, Elhard and Heggs, filed Apr. 26, 2000.

FIELD OF INVENTION

The present invention relates to objects (for example, golf balls) which have an outer surface that contains solvent-activated and solvent-sensitive color-forming compositions, methods of making such objects and methods of using such objects.

BACKGROUND OF THE INVENTION

Prolonged exposure to, or immersion in, certain solvents (e.g., water) can adversely affect the physical, chemical and mechanical properties of some polymer materials, composite materials, and synthetic construction materials. For example, the exterior of golf balls typically consists of one or more polymer materials. A golf ball that has been submerged in a water hazard for an extended period of time will exhibit inferior flight characteristics compared to a new golf ball, despite the superficial similarity in appearance of the two golf balls (*Golf Digest*, September 1996). In some instances, the diminished performance of certain materials caused by prolonged exposure to a solvent is temporary and mostly reversible if the solvent is removed by drying the affected materials. In other situations, the effects are permanent and performance is irreversibly damaged. In certain situations, any exposure to a solvent, however brief, may create performance concerns. Thus, there is a need for a color-based indicator that can be incorporated into various solvent-sensitive materials which will alert the user to the possibility that the performance of the materials has been compromised by exposure to, or immersion in, a given solvent. Ideally, color formation would be either reversible or permanent based on different formulations of the indicator and the material it is combined with.

Several water-sensitive color systems currently exist. U.S. Pat. No. 5,130,290, Tanimoto, issued Jul. 14, 1992, discloses a water-sensitive coloring sheet which includes a substrate and a water-sensitive coloring layer containing an unencapsulated color developing material that reacts with a dye when the coloring layer is wetted. The inclusion of a desensitizing material in this system results in a reversible color formation system (i.e., the removal of water results in the removal of the color). U.S. Pat. No. 5,501,945, Kanakkanatt, issued Mar. 26, 1996, discloses the concept of a reversible system in which water sensitive chemichromic dyes are incorporated into polymers used for various packaging applications. U.S. Pat. Nos. 5,823,891 and 5,938,544, both to Winskowicz, issued Oct. 20, 1998 and Aug. 17, 1999, respectively, disclose a color-forming system for use with golf balls which utilizes a water permeable covering over the core of a golf ball, and a water soluble pelletized or microencapsulated colored dye near or within the covering.

All of the discussed systems require some type of colored dye which when subjected to the correct stimulus undergoes a color change. Such dyes must often be processed, i.e., pelletized or microencapsulted, before they can be incorporated into a particular material. Processing dyes in this manner adds difficulty and expense to the process of creating a water-activated color-forming material. Furthermore, these dyes may be removed by simply bleaching the colored material.

SUMMARY OF THE INVENTION

The present invention provides an object which, in its outer surface, contains a color-forming composition which comprises a solvent-absorbing material that is generally a polymer; a color-former compounded with the solvent-absorbing material, where the color-former functions as a metal chelating agent; and metal ions capable of forming a chelate complex with the color-former as the solvent-absorbing material absorbs a solvent, resulting in a detectable color change of the composition. These components are present in an effective amount such that when the outer surface of the object is exposed to a solvent for at least two days, a distinct color change is observable and this color change is generally irreversible. The present invention also provides a method for indicating exposure of the color-forming composition to a solvent, wherein the color-forming composition is to be used on the outside surface of objects.

Solvent-absorbing polymers suitable for use in the present invention include, for example: polyethylene acrylic acid, polyethylene methacrylic acid, and copolymers thereof; terpolymers of polyethylene, an acrylic acid and an acrylate; polyurethane; poly-(acrylonitrile-butadiene-styrene); polyvinylchloride; polypropylene copolymer; polystyrene; silicon elastomers; organic rubbers; and combinations thereof.

Preferred metal ions which are suitable for use in the present invention are selected from the group consisting of $Na^+$, $Li^+$, $Zn^{2+}$, $Fe^{3+}$, $Fe^{2+}$, $Ca^{2+}$, $Mg^{2+}$, $Li^+$, $Ti^{2+}$, $Ti^{4+}$, $Mn^{2+}$, and combinations thereof.

Two types of color-formers may be used in the present invention: one which produces a permanent color change that is not reversed by removal of the solvent from the solvent absorbing material; and another which provides for a reversible color change when the absorbed solvent is removed from the outer covering of the object.

The color-formers which are used to produce the permanent color change are present in an amount of from about 0.1%, by weight to about 2.5%, by weight. They are generally 1,2-dihydroxybenzene derivatives which include, but are not limited to 1,2-dihydroxybenzene, 3-methylcatechol, 4-methylcatechol, 4,5-dihydroxy-1,3-benzenedisulfonic acid disodium salt and 1,2,3-trihydroxybenzene and mixtures thereof Reversible color-formers are also present in an amount of from about 0.1% to about 2.5%, by weight. They are typically fluoran derivatives substituted with at least one amine group at positions 3 and/or 6. Examples include, but are not limited to, 3-diethylamino-6-methyl-fluoran, 3-dimethylamino-6-methyl-fluoran, 3-dimethylamino-6-methyl-7-anilinofluoran, 2-anilino-3-methyl-6-dibutylaminofluoran, 3-diethylamino-6-methyl-7-anilinofluoran, and 2-anilino-3-methyl-6-diethylaminofluoran and mixtures thereof.

The reversible color-formers may be augmented with a fixative that renders the reversible color change more permanent, depending on the cumulative degree of reaction between the components. The fixatives of the present invention are generally phenolic-based compounds, such as salicylic acid or bisphenol-A, the acetate derivatives thereof and mixtures thereof.

The color-forming compositions of the present invention are white or colorless after initial processing and do not change color until solvent is absorbed. These color-forming compositions are essentially "aquachromic," meaning that color change occurs upon exposure to water, but are not "hydrochromic," because exposure to moderate humidity alone does not initiate a color change. Once the color change has occurred, the color-forming compositions of this invention are generally unaffected by treatment with typical solutions designed for color removal for extended periods of time. The color-forming compositions of the present invention can have multiple uses, including use as an outer covering for golf balls, whereby prolonged exposure of the color-forming composition to a liquid, such as water, results in a detectable color change of the composition.

BRIEF DESCRIPTION OF THE FIGURES

FIG. 1 depicts a color formation vs. time plot for the irreversible color-forming embodiment of the present invention. In a typical experimental procedure, samples of each composition are compounded on a 2-roll mill at about 104° C. (220° F.), compression molded into a plaque form, cut to about 2×5 inches size, weighed on an analytical scale, and the initial color measured using a X-rite (L,a,b values). The samples are then immersed in water. Periodically, samples are removed, reweighed, and the color remeasured.

DETAILED DESCRIPTION OF THE INVENTION

In general, the present invention provides a color-forming composition that includes a solvent-absorbing material, a chelating agent or "color-former" that is compounded with the solvent-absorbing material, and a source of metal ions. The metal ions form a chelate complex with the chelating agent or color-former as a solvent (e.g. water) is absorbed by the solvent-absorbing material, resulting in a color change of the composition. For example, the solvent-absorbing material may change from white to green, brown, or black.

The color-forming compositions of the present invention are white or colorless after initial processing, and do not change color until a solvent is absorbed by the solvent-absorbing material. Furthermore, the present invention provides color-forming compositions that are essentially "aquachromic" meaning that color change occurs upon exposure to water, but that are not "hydrochromic" because exposure to moderate humidity alone does not initiate a color change. Finally, once the color change has occurred, the color-forming compositions of this invention are unaffected by treatment with typical solutions designed for color removal (e.g., 3% $H_2O_2$, 1M HCl, Alconox, Clorox Bleach) for extended periods of time. Long-term exposure to hazardous solvents such as bleach will ultimately degrade the polymer itself, thus the polymer will break down before the color change can be removed.

Applications for water-activated and water-sensitive color-forming compositions include a number of uses that depend on moisture as the stimulii and color change as the response. For example, one useful coating application for the "reversible" form could be for aircraft de-icing. A coating applied to airplane exteriors would indicate the presence of water on the wings and other horizontal surfaces. The indicator would be used to determine if de-icing is necessary or if the de-icing has been successful in melting the ice, and eliminating the water.

Another application would be for moisture indication in packaging. For example, a color change window or panel on the bag or bottle could indicate that the product has been compromised by moisture, an important criteria for dry flowable powder formulations. The indicator could be used to determine shelf-life of expensive medications (chemotherapy, AIDS drugs, etc.) and when they should be discarded, greatly reducing waste.

A subset of the packaging application would be where the indicator is placed on/in a label, which could be attached to a product, such as containers for hygroscopic chemical reagents. In this case the indicator is not integrated directly into the object, but is attached to the exterior or placed in the nearby vicinity (for example, bulk shipping containers).

A specific embodiment of the color change technology could be in a moisture-sensitive paint or coating that changes color after exposure to water. Such a paint or coating could be useful for interior basement walls, indicating where water is permeating from the outside or that some degree of flooding had occurred and that some structural problems could now exist. Such a paint could be applied to the interior of fuel storage tanks to enable the presence of wet-fuel to be detected (through visual inspection through a port).

The specific paint application will be explained in more detail, by way of example. Where the substrate is a paint or coating, the color formation can either be generated in the layer(s) beneath the paint, with the colored complex migrating through the paint, or one component (e.g. the color-former) can be present in the material being painted and the other component (e.g. the metal ion) can be present in the paint. Once adequate moisture penetrates through the paint to the material below, the metal ion will be carried back to the color-former and color development will take place upon complexation/chelation of the color-former with the metal ion. This ability to deploy the metal ion in one layer and the color-former in another (perhaps not even adjacent) layer offers flexibility for a variety of materials applications.

In the case of golf balls for example, the color-former can be incorporated into the coverstock, and the color developer can be included in one or more paint or coating layers. Typically, polyurethane golf ball coverstock has limited UV stability, and is painted with one to two coats of a white pigmented epoxy based or polyurethane based paint, or the combination thereof Alternatively, ionomer golf ball coverstock may be covered with a primer coat, which may or may not contain additives. Both systems are typically covered with a final clear topcoat. These scenarios offer a number of opportunities for deployment of color-forming components, depending on the specific product specifications required (i.e. humidity stability, UV stability etc.). This is analogous to the deployment of optical brighteners in golf balls, where they may be incorporated into the coverstock, into the primer layer, or into the clear topcoat.

The solvent-absorbing substance is typically a polymer (ionomer) comprising generally at least 90% by weight of the composition excluding fillers. Examples of suitable polymers include polyethylene acrylic acid or polyethylene methacrylic acid, or terpolymers of polyethylene and acrylic or methacrylic acid, and an acrylate such as methyl acrylate or butyl accrylate is replaced with other polymers including polyurethane, poly-(acrylonitrile-butadiene-styrene), polyvinyl chloride, polypropylene-copolymer, and polystyrene or combinations thereof These polymers are widely used in a number of industrial and packaging applications. In alternate embodiments, the solvent absorbing material may be paint, or synthetic construction material such as polyvinyl chloride, silicone elastomers, or organic rubbers.

The solvent may either be an inorganic solvent, an organic solvent or water. Inorganic solvents include ammonium hydroxide, hydrogen peroxide, hydrochloric acid, or hypochlorite (bleach); or an organic solvent such as ethanol, ethyl acetate, toluene, xylene, or diesel fuel. Preferred organic solvents are those exhibiting some degree of polarity such as ethyl acetate and tetrahydrofuran. Most commonly the triggering solvent will be water.

The source of metal ions may vary widely in alternative embodiments. For example, in one embodiment, the source of metal ions is supplied by the solvent itself In another embodiment, the source of metal ions is the solvent-absorbing material. For example, the $Na^+$, $Li^+$, or $Zn^{+2}$ ions which are already present in the polymers/ionomers previously mentioned. In yet another embodiment, the source of the metal ions is any one of a variety of metal salts. In alternative embodiments, the metal ions themselves are $Zn(+2)$, $Fe(+2)$, $Fe(+3)$, $Na(+)$, $Ca(+2)$, $Mg(+2)$, $Li(+)$, $Ti(+2)$, $Ti(+4)$ $Mn(+2)$, or any other suitable metal ion, both as isolated cations and with other coordinating ligands such as hydrate, acetate, or ester forms(e.g., Zn(II) 3,5-di-t-butylsalicylate) or as solid forms such as zinc oxide, alumina or titania.

In embodiments of this invention where color formation is irreversible, the color-formers are present in an amount of from about 0.1% to about 2.5%, by weight. The irreversible color-formers are generally 1,2-dihydroxy aromatic compounds, which include but are not limited to 3-methylcatechol, 4-methylcatechol, and 4,5-dihydroxy 1,3-benzenedisulfonic acid disodium salt(Tiron), or alternatively, 1,2,3-trihydroxybenzene(pyrogallol).

In embodiments of this invention where color formation is reversible, the color-formers are present in an amount of from about 0.1% to about 2.5%, by weight. The reversible color-formers are typically fluoran derivatives substituted with at least one amine group at positions 3 and/or 6. Examples include, but are not limited to 3-diethylamino-6-methyl-fluoran, 3-dimethylamino-6-methyl-fluoran, 3-dimethylamino-6-methyl-7-anilinofluoran, 2-anilino-3-methyl-6-dibutylaminofluoran, 3-diethylamino-6-methyl-7-anilinofluoran, and 2-anilino-3-methyl-6-diethylaminofluoran and mixtures thereof Such compounds are also disclosed in U.S. Pat. Nos. 3,669,711, Kimura et al., issued Jun. 13, 1972; U.S. Pat. No. 3,819,396, Vincent et al. issued Jun. 25, 1974; U.S. Pat. No. 3,821,010, Vincent et al., issued Jun. 28, 1974; U.S. Pat. No. 4,302,393, Garner et al., issued Nov. 24, 1981; and U.S. Pat. No. 6,071,853, Kirk et al., issued Jun. 6, 2001; which are herein incorporated by reference. A preferred fluoran dye is 3

IV

-dietheylamino-6-methylfluoran(see IV; tradename PERGASCRIPT BLACK I-R).

In another embodiment of the present invention, the reversible color-forming composition is augmented by a fixative that renders the color development more or less permanent, depending on the degree of the secondary reaction, which is usually a function of immersion time. Examples of fixatives that have shown utility in the present invention include phenolic-based compounds such as those employed in carbonless paper applications. However, most of these are designed for compatibility with hydrocarbon oil dispersants and have limited water solubility. For the compositions of the present invention, the proper balance of polymer or substrate compatibility and water solubility are necessary to achieve the desired effect.

In addition, no direct color-forming reaction should occur between the components during any mixing, compounding, processing, molding or subsequent treatment steps. Color formation must only take place upon immersion in solvent, such as water. Given these restrictions, we have found that the preferred fixatives are derivatives of either salicylic acid or alternatively derivatives of bisphenol-A. The preferred embodiments for the present invention are typically not used in the carbonless paper systems, since they are present in their ester forms and must hydrolyze to achieve activity for use in this application.

The preferred fixatives of this invention are bisphenol diacetate, and acetylsalicylic acid. Other fixatives include esters such as salicylsalicylate, lactones such as phenolphthalein, or other substances containing carboxyl and/or hydroxyl protecting groups. These formulations may also include a source of $H^+$ or $OH^-$ ions to aid in the hydrolysis of the fixative. Examples of such $H^+$ or $OH^-$ sources include salicylic acid, citric acid, or any number of other acidic or basic materials.

In a preferred embodiment of the present invention, the color-forming composition is used as the outer cover for golf balls, which is typically white. The solvent absorbing material is the polymer polyethylene methacrylic acid ionomer containing about 5% titanium dioxide filler(tradename SURLYN) or the polymer polyethylene acrylic acid ionomer( tradename IOTEK), the color-former or chelating agent is 1,2-dihydroxybenzene(also known as catechol), and the metal ions are zinc (+2) from zinc acetate. In the preferred embodiment, the polymer, the color-former, and the Zn(+2) ions are compounded to form the outer covering of the golf ball.

Figure 1:
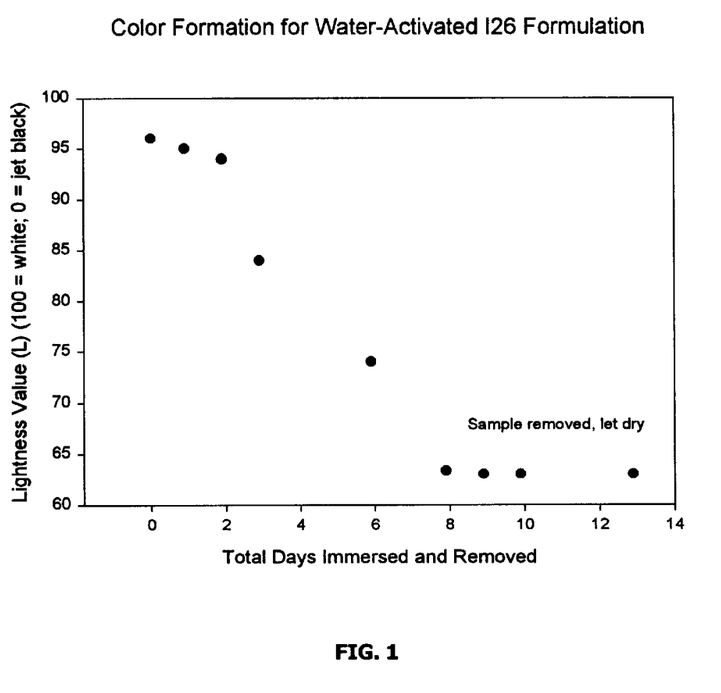

In another embodiment, only catechol is compounded with the polymer and color-former, and the source of metal ions is derived from the ionomer itself, the solvent, or from another source. The preferred solvent is water, and when a golf ball coated with the color-forming composition of the present invention is submersed in water for an extended period of time(e.g. from about two to about eight days), the polymer absorbs water, thereby moving the Zn(+2) ions (individually or complexed with another material) into contact with the color-former, or vice-versa. The metal ions and the color-former form a chelate complex which results in a permanent darkening of the outer cover of the golf ball. FIG. 1 provides a representative color formation vs. time plot for the preferred embodiment. In this embodiment, the darkened color cannot be reversed if the water is removed from the outer cover.

Figure 2A:
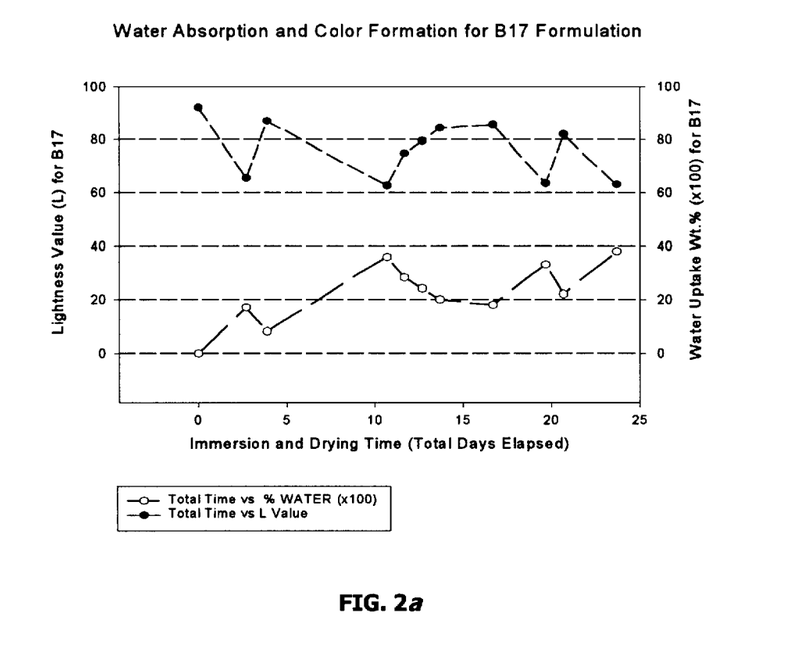
FIG. 2a depicts a color formation vs. time plot for the reversible color-forming embodiment of the present invention before an extrusion check for thermo-oxidative stability. See the legend for FIG. 1 for a description of analytical test procedures.
Figure 2B:
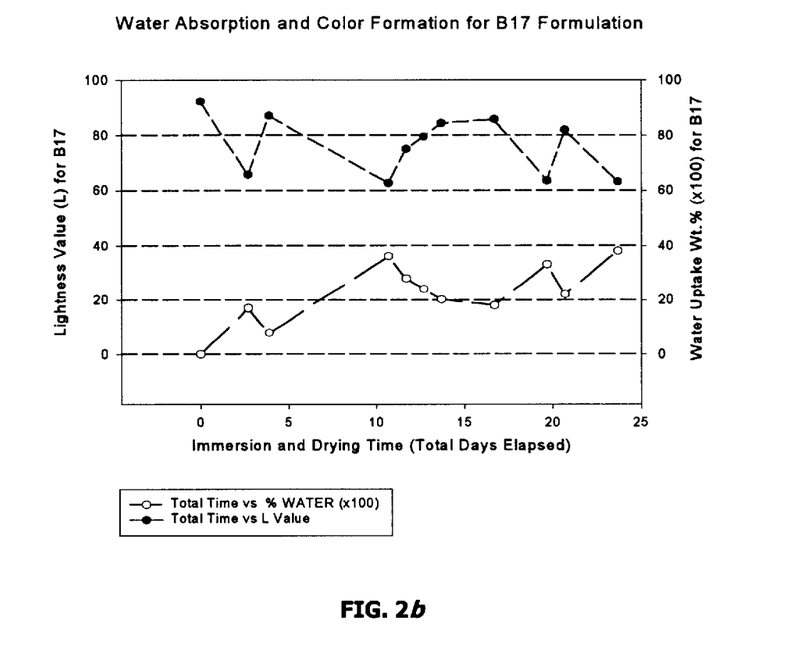
FIG. 2b depicts a color formation vs. time plot for the reversible color-forming is embodiment of the present invention after an extrusion check for thermo-oxidative stability. See the legend for FIG. 1 for a description of analytical test procedures.
Figure 3:
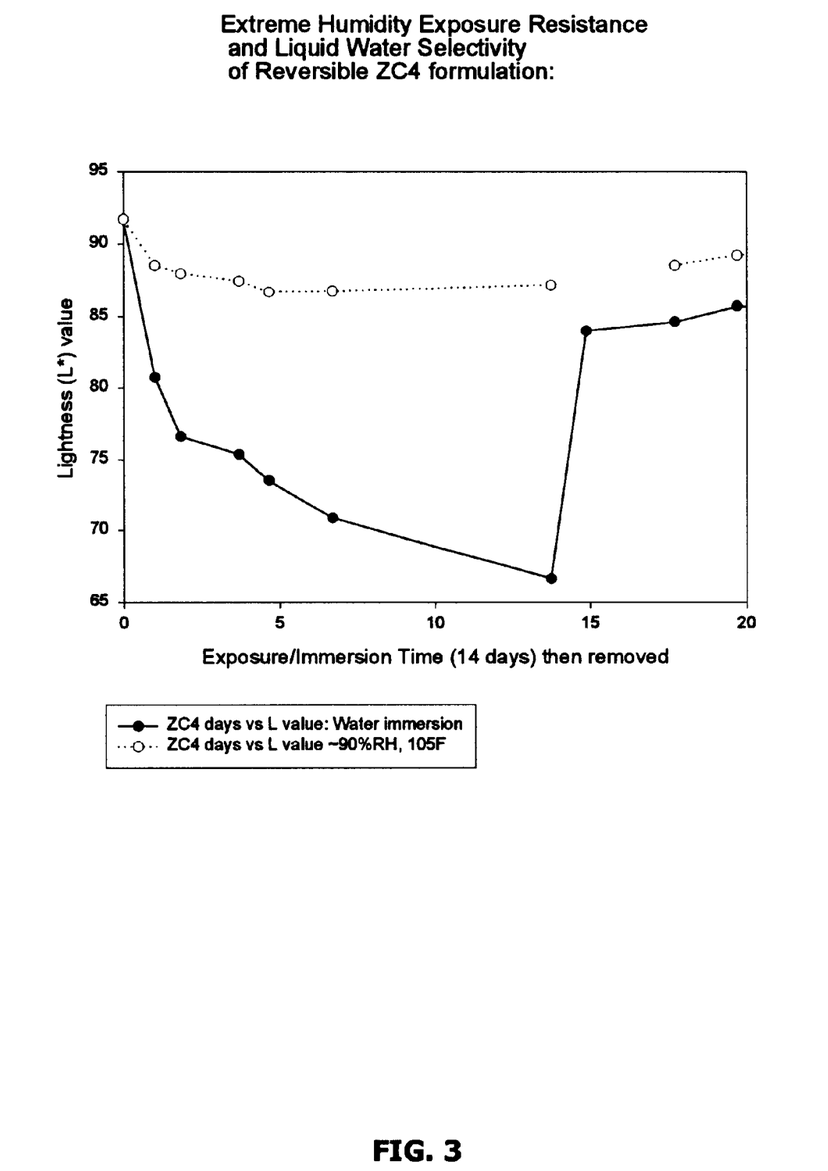
FIG. 3 depicts a color formation vs. time plot for the reversible color-forming embodiment of the present invention illustrating the excellent humidity resistance at elevated temperature (~90% RH, 105F.). For comparison, the corresponding color formation observed in liquid water is included. In this example, the polymer substrate is an ionomer blend (Iotek) composition which has been compounded and injection molded into golf balls. After molding, the golf ball substrates were placed alternatively in liquid water or elevated temperature/humidity conditions for a period of 14 days (in this case) and subsequently removed to dry.
Figure 4:
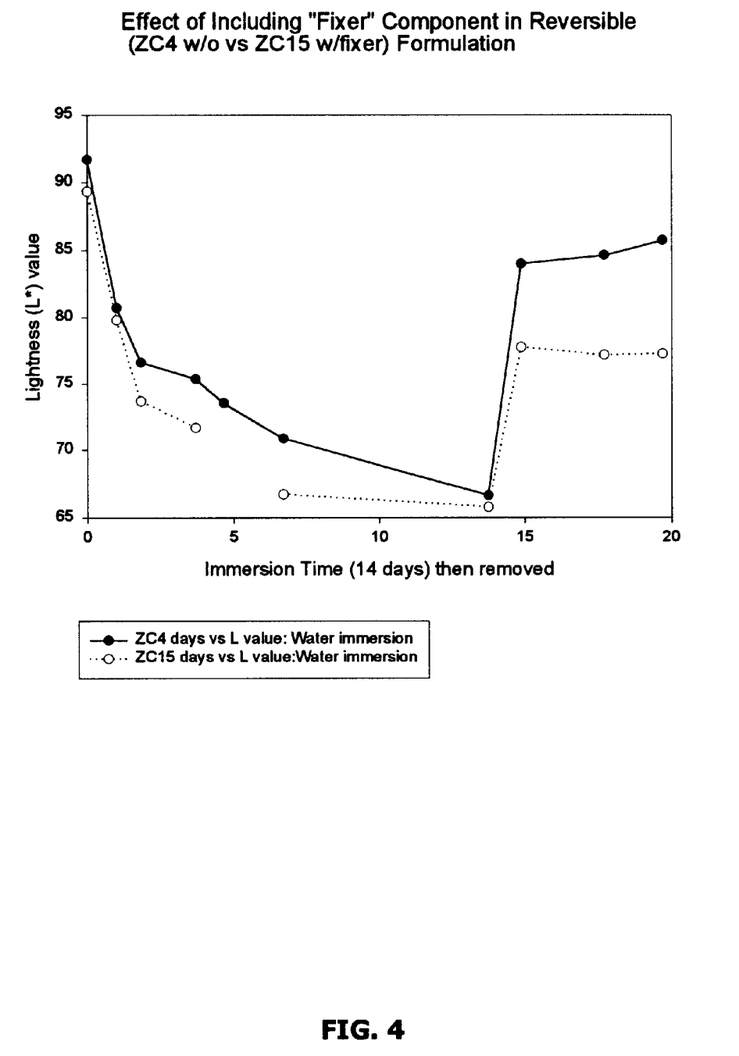
FIG. 4 depicts a color formation vs. time plot for the reversible color-forming embodiment of the present invention in which a fixative has been added (designated as ZC15), in comparison to the ZC4 formulation without the fixative. The substrate is an injection molded ionomer golf ball as described in FIG. 3. The final color achieved after removal and drying is darker for the ZC15 system. Incorporation of such a fixative permits conversion of the reversible color-forming system toward an irreversible one, depending on the relative loading and time of immersion.

Not being bound by theory, it is thought that catechol complexed with $Fe(^{+3})$ may have the following expected structure(s)(I and II) where complex formation can lead to associated extended networks:

Alternatively, the chelate-complex may be present in a form where the additional ligands(e.g. acetate and hydrate forms) also participate, as shown for the zinc(II) diacetate dihydrate-catechol complex(III) below:

Another preferred formulation for this invention includes: polyethylene acrylic acid polymer/ionomer containing about 5% titanium dioxide filler resin; about 0.1% to about 2.5%, by weight of PERGASCRIPT BLACK IR; and about 0.1% to about 2.5% zinc acetate. This embodiment also exhibits thermo-oxidative stability at compounding temperatures of at least 80° C. and extrusion temperatures of at least 190° C. FIG. 2a and FIG. 2b provide color formation versus time plots for the reversible embodiment of the present invention before and after an extrusion check for thermo-oxidative stability.

The performance of the color formation in a particular polymer system can be controlled by the type and loading of both the color-former and the corresponding metal ion, where performance includes rate of color formation, final color level achieved, stability(shelf-life) under elevated temperature and humidity conditions, as desired. Another preferred formulation for this invention includes: polyethylene methacrylic acid polymer/ionomer or polymer blend(e.g., 80% SURLYN 8940, 20% SURLYN 9910) containing about 5% titanium dioxide filler resin; or polyethylene acrylic acid ionomer or ionomer blend(e.g. 80% IOTEK 8030, 20% IOTEK 7010) and from about 0.1% to 2.5% 1,2-dihydroxybenzene, and from about 0.1% to 2.5% zinc acetate. The optimum color formation in these systems is achieved with a stoichiometric ratio of chelating agent and metal ion.

Adding greater amounts of color-forming components (i.e., chelating agent and metal ions) results in increased rapidity and intensity of color formation. Substitution of certain components also increases rapidity and intensity of color formation; for example, in one embodiment Mg(II) acetate is used place of Zn(II) acetate to create a more rapid color change. In other embodiments of the present invention, certain adjuvants are added to the composition to enhance or inhibit the water absorption of the base polymer and modify the color formation process. These additives include, but are not limited to, pentaerythritol, ethylene glycol, polyethylene glycol, and polyacrylic acid.

Another preferred embodiment of the present invention exhibits thermo-oxidative stability at compounding temperatures of at least 90° C. and extrusion temperatures of at least 180° C. This embodiment also exhibits stability against premature color formation under elevated temperature and humidity conditions. For example, representative formulations exposed to 40–45° C. (104–113° F.) and 75% RH (relative humidity) in an environmental chamber for a period of 24 hours show no discernable color change(less than about 1 L unit). Similarly, materials exposed to milder, ambient-like conditions(e.g., about 72° F./45% RH) show no discernable change for at least a week, compared to the substantial color development(40–50 L units) over the same period of water immersion.

One method of making a color-forming composition of the present invention includes the steps of: (i) providing a solvent-absorbing material, a color-former, and a source of metal ions; (ii) dry blending the solvent-absorbing material, the color-former, and the metal ions in a batch process; and (iii) compounding the batch in an extruder or other suitable mixing device. An alternative method of making a color-forming composition, includes the steps of (a) providing a solvent-absorbing material, a color-former, and a source of metal ions; and (ii) metering the solvent-absorbing material, the color-former, and the metal ions into an extruder or other continuously compounding device. Another method of making a color-forming composition includes dry blending or continuously metering the active ingredients into the final processing step, provided that the final processing step has a minimum amount of mixing capability such as provided by an injection molder or an extruder.

A preferred method for making a color-forming composition, which utilizes a "masterbatch" includes the steps of: (i) providing a solvent-absorbing material, a color-former, and a source of metal ions; and (ii) at the final fabrication step, adding the color-former and the source of metal ions to the solvent absorbing material at a level higher than that required for the desired final concentration of the color-former and the source of metal ions in the solvent-absorbing material. For example, a pigment masterbatch may contain 40% pigment by weight, while the final product may only contain 4% or less. In this embodiment, the masterbatch is mixed with the base resin at the final fabrication step such as injection molding in a ratio that results in the final desired additive amount.

The benefits of the masterbatch approach include the following: (i) additives can be handled in the "neat" or 100% concentrated state at a remote location for safety or other reasons such as the need for special handling equipment(as in the case of liquid additives) or the desire to minimize the risk of contamination of other products; (ii) the masterbatches improve dispersion of the additive in the final product by being processed twice(many final fabrication processes typically optimize the plastication or melting of the polymer rather than optimize mixing); (iii) additives are sensitive to environmental degradation such as moisture or light, the small volume of masterbatch can be more easily protected and handled; (iv) a resin of different characteristics can be used for the masterbatch and the final product to improve processing. For example, the masterbatch resin could be lower in viscosity to increase the amount of additive it can contain while the resin for the final part may be higher in viscosity to improve mechanical properties; and (v) masterbatches can use very aggressive and expensive mixing equipment such as twin screw extruders while the final product can use equipment suited to the formation of the part.

While the above description contains many specificities, these should not be construed as limitations on the scope of the invention, but rather as exemplification of preferred embodiments. Numerous other variations of the present invention are possible, and it is not intended herein to mention all of the possible equivalent forms or ramifications of this invention. Various changes may be made to the present invention without departing from the scope of this invention

What is claimed is:

1. An object which, in its outer surface contains a color-forming composition which comprises:

a. a solvent-absorbing material;
   b. a color former compounded with said solvent-absorbing material, wherein said color former functions as a metal chelating agent; and
   c. a source of metal ions compounded with said solvent-absorbing material or said solvent-absorbing material containing the metal ions;
      and wherein metal ions from said source of metal ions are capable of forming a chelate complex with said color former as said solvent-absorbing material absorbs said solvent, resulting in a detectable color change of said composition;
      wherein the solvent-absorbing material is a polymer selected from the group consisting of polyethylene acrylic acid, polyethylene methacrylic acid, and copolymers thereof; terpolymers of polyethylene, an acrylic acid and an acrylate; polyurethane; poly-(acrylonitrile-butadiene-styrene); polyvinylchloride; polypropylene copolymer; polystyrene; polyurethane; silicon elastomers; organic rubbers; and combinations thereof;
      wherein said metal ions are selected from the group consisting of $Na^+$, $Li^+$, $Zn^{2+}$, $Fe^{3+}$, $Fe^{2+}$, $Ca^{2+}$, $Mg^{2+}$, $Li^+$, $Ti^{2+}$, $Ti^{4+}$, $Mn^{2+}$, and combinations thereof;
      wherein said color former produces a permanent color change which is not reversed by removal of said solvent from said solvent absorbing material; and
      wherein said color former is a 1,2-dihydroxybenzene derivative.

2. An object which, in its outer surface contains a color-forming composition which comprises:

a. a solvent-absorbing material;
   b. a color former compounded with said solvent-absorbing material, wherein said color former functions as a metal chelating agent; and
   c. a source of metal ions compounded with said solvent-absorbing material or said solvent-absorbing material containing the metal ions;
      and wherein metal ions from said source of metal ions are capable of forming a chelate complex with said color former as said solvent-absorbing material absorbs said solvent, resulting in a detectable color change of said composition,
      wherein the solvent-absorbing material is a polymer selected from the group consisting of polyethylene acrylic acid, polyethylene methacrylic acid, and copolymers thereof; terpolymers of polyethylene, an acrylic acid and an acrylate; polyurethane; poly-(acrylonitrile-butadiene-styrene); polyvinylchloride; polypropylene copolymer; polystyrene; polyurethane; silicon elastomers; organic rubbers; and combinations thereof;
      wherein said metal ions are selected from the group consisting of $Na^+$, $Li^+$, $Zn^{2+}$, $Fe^{3+}$, $Fe^{2+}$, $Ca^{2+}$, $Mg^{2+}$, $Li^+$, $Ti^{2+}$, $Ti^{4+}$, $Mn^{2+}$, and combinations thereof;
      wherein said color former produces a permanent color change which is not reversed by removal of said solvent from said solvent absorbing material; and
      wherein said color former is selected from the group consisting of 1,2-dihydroxybenzene, 3-methylcatechol, 4-methylcatechol, 4,5-dihydroxy-1,3-benzenedisulfonic acid disodium salt and 1,2,3-trihydroxybenzene and mixtures thereof.

3. The object of claim 2 wherein said color former is 1,2-dihydroxybenzene and is present in the composition at from about 0.1% to about 2.5%, by weight.

4. An object which, in its outer surface contains a color-forming composition which comprises:
   a. a solvent-absorbing material;
   b. a color former compounded with said solvent-absorbing material, wherein said color former functions as a metal chelating agent; and
   c. a source of metal ions compounded with said solvent-absorbing material or said solvent-absorbing material containing the metal ions;
   and wherein metal ions from said source of metal ions are capable of forming a chelate complex with said color former as said solvent-absorbing material absorbs said solvent, resulting in a detectable color change of said composition;
   wherein the solvent-absorbing material is a polymer selected from the group consisting of polyethylene acrylic acid, polyethylene methacrylic acid, and copolymers thereof; terpolymers of polyethylene, an acrylic acid and an acrylate; polyurethane; poly-(acrylonitrile-butadiene-styrene); polyvinyl-chloride; polypropylene copolymer; polystyrene; polyurethane; silicon elastomers; organic rubbers; and combinations thereof;
   wherein said metal ions are selected from the group consisting of $Na^+$, $Li^+$, $Zn^{2+}$, $Fe^{3+}$, $Fe^{2+}$, $Ca^{2+}$, $Mg^{2+}$, $Li^+$, $Ti^{2+}$, $Ti^{4+}$, $Mn^{2+}$, and combinations thereof;
   wherein said color former is a substituted fluoran derivative with at least one amine group at positions 3 and 6:

5. The object of claim 4 wherein R1 and R2 of the amine group are alkyl groups containing from one to six carbon atoms independently.

6. The object of claim 5 wherein said color former is selected from the group consisting of 3-diethylamino-6-methyl-fluoran, 3-dimethylamino-6-methyl-fluoran, 3-dimethylamino-6-methyl-7-anilinofluoran, 2-anilino-3-methyl-6-dibutylaminofluoran, 3-diethylamino-6-methyl-7-anilinofluoran, and 2-anilino-3-methyl-6-diethylaminofluoran and mixtures thereof.

7. The object of claim 4 wherein a fixative is added to retard reversal of said color change and wherein said fixative is present at from about 0.1% to about 2.5%, by weight.

8. The object of claim 7 wherein the fixative is a phenolic-based compound.

9. The object of claim 8 wherein the fixative is salicylic acid or bisphenol-A, the acetate derivatives thereof and mixtures thereof.

10. An object which, in its outer surface contains a color-forming composition which comprises:
    a. a solvent-absorbing material;
    b. a color former compounded with said solvent-absorbing material, wherein said color former functions as a metal chelating agent; and
    c. a source of metal ions compounded with said solvent-absorbing material or said solvent-absorbing material containing the metal ions;
    and wherein metal ions from said source of metal ions are capable of forming a chelate complex with said color former as said solvent-absorbing material absorbs said solvent, resulting in a detectable color change of said composition;
    wherein said solvent-absorbing material is polyethylene methacrylic acid; said color-former is from about 0.1% to about 2.5%, by weight of a 1,2-dihydroxybenzene derivative; and said metal ion is $Zn^{2+}$, in an amount of from about 0.1% to about 2.5%, by weight.

11. The object of claim 10 wherein the object is a golf ball.

12. A solvent-activated, color-forming composition, comprising:
    a. a solvent-absorbing material;
    b. a color former compounded with said solvent-absorbing material, wherein said color farmer functions as a metal chelating agent; and
    c. a source of metal ions compounded with said solvent-absorbing material or said solvent-absorbing material containing the metal ions;
    and wherein metal ions from said source of metal ions are capable of forming a chelate complex with said color former as said solvent-absorbing material absorbs a solvent, resulting in a detectable color change of said composition;
    wherein said metal ions are selected from the group consisting of $Na^+$, $Li^+$, $Zn^{2+}$, $Fe2+$, $Fe^{3+}$, $Ca^{2+}$, $Mg^{2+}$, $Li^+$, $Ti^{2+}$, $Ti^{4+}$, $Mn^{2+}$, and combinations thereof and wherein said metal ions are present at from about 0.1% to about 2.5%, by weight; wherein said color former produces a permanent color change which is not reversed by removal of said solvent from said solvent absorbing material; and
    wherein said color former is a 1,2-dihydroxybenzene derivative and wherein said color former is present at from about 0.1% to about 2.5%, by weight.

13. The composition of claim 12 wherein said color former is selected from the group consisting of 1,2-dihydroxybenzene, 3-methylcatechol, 4-methylcatechol, 4,5-dihydroxy-1,3-benzenedisulfonic acid disodium salt and 1,2,3-trihydroxybenzene and mixtures thereof.

14. A solvent-activated, color-forming composition, comprising:
    a. a solvent-absorbing material;
    b. a color former compounded with said solvent-absorbing material, wherein said color former functions as a metal chelating agent; and
    c. a source of metal ions compounded with said solvent-absorbing material or said solvent-absorbing material containing the metal ions;
    and wherein metal ions from said source of metal ions are capable of forming a chelate complex with said color former as said solvent-absorbing material absorbs a solvent, resulting in a detectable color change of said composition;
    wherein said metal ions are selected from the group consisting of $Na^+$, $Li^+$, $Zn^{2+}$, $Fe2+$, $Fe^{3+}$, $Ca^{2+}$, $Mg^{2+}$, $Li^+$, $Ti^{2+}$, $Ti4+$, $Mn^{2+}$, and combinations thereof and wherein said metal ions are present at from about 0.1% to about 2.5%, by weight;
    wherein said color change is reversible when the absorbed solvent is removed from said composition; and wherein said color former is a substituted fluoran derivative with at least one amine group at positions 3 and 6, wherein $R_1$ and $R_2$ of the amine group are alkyl groups containing from one to six carbon atoms independently and wherein said color former is present at from about 0.1% to about 2.5%, by weight.

15. The composition of claim 14 wherein said color former is selected from the group consisting of 3-diethylamino-6-methyl-fluoran, 3-dimethylamino-6-methyl-fluoran, 3-dimethylamino-6-methyl-7-anilinofluoran, 2-anilino-3-methyl-6-dibutylaminofluoran, 3-diethylamino-6-methyl-7-anilinofluoran, and 2-anilino-3-methyl-6-diethylaminofluoran and mixtures thereof.

16. The composition of claim 14 wherein a fixative is added to retard reversal of said color change and wherein said fixative is present at from about 0.1% to about 2.5%, by weight.

17. The composition of claim 16 wherein said fixative is a phenolic-based compound.

18. The composition of claim 17 wherein said fixative is selected from salicylic acid, bisphenol-A, acetate derivatives of salicyclic acid and bisphenol A, and mixtures thereof.

19. A method for indicating exposure of a color-forming composition to a solvent, said method comprising:

(a) providing a solvent;
(b) providing a solvent-absorbing material;
(c) compounding a color-former which functions as a metal chelating agent, with said solvent-absorbing material;
(d) providing a source of metal ions compounded with said solvent-absorbing material or said solvent-absorbing material containing the metal ions;
and wherein metal ions from said source of metal ions are capable of forming a chelate complex with said color former as said solvent-absorbing material absorbs said solvent, resulting in a detectable color change of said composition; and
(e) contacting said solvent-absorbing material with said solvent,
whereby as said solvent is absorbed by said solvent-absorbing material, said metal ions contact and chelate with said color former resulting in a detectable color change of said composition; wherein said solvent is water; and
said solvent absorbing material is a polymer selected from the group consisting of polyethylene acrylic acid, polyethylene methacrylic acid, and copolymers thereof;
said color former is a 1,2-dihydroxybenzene derivative selected from the group consisting of 1,2-dihydroxybenzene, 3-methylcatechol, 4-methylcatechol, 4,5-dihydroxy-1,3-benzenedisulfonic acid disodium salt and 1,2,3-trihydroxybenzene and mixtures thereof; and said metal ion is $Zn^{2+}$.

20. A method for indicating exposure of a color-forming composition to a solvent, said method comprising:

(a) providing a solvent;
(b) providing a solvent-absorbing material;
(c) compounding a color-former which functions as a metal chelating agent, with said solvent-absorbing material;
(d) providing a source of metal ions compounded with said solvent-absorbing material or said solvent-absorbing material containing the metal ions;
and wherein metal ions from said source of metal ions are capable of forming a chelate complex with said color former as said solvent-absorbing material absorbs said solvent, resulting in a detectable color change of said composition; and
(e) contacting said solvent-absorbing material with said solvent,
whereby as said solvent is absorbed by said solvent-absorbing material, said metal ions contact and chelate with said color former resulting in a detectable color change of said composition; wherein said solvent is water; and
said solvent absorbing material is a polymer selected from the group consisting of polyethylene acrylic acid, polyethylene methacrylic acid, and copolymers thereof;
said color former is a substituted fluoran derivative with at least one amine group at positions 3 and 6, wherein R1 and R2 of the amine group are alkyl groups containing from one to six carbon atoms independently; and said metal ion is $Zn^{2+}$.

21. The method of claim 20 wherein a fixative is added to said composition, said fixative comprising acetylsalicylic acid or bisphenol diacetate and mixtures thereof.

* * * * *